United States Patent [19]
Hashimoto et al.

[11] Patent Number: 5,714,357
[45] Date of Patent: Feb. 3, 1998

[54] PROCESS FOR PRODUCING OPTICALLY ACTIVE α-HYDROXYCARBOXYLIC ACID HAVING PHENYL GROUP

[75] Inventors: Yoshihiro Hashimoto; Takakazu Endo; Koji Tamura; Yuji Hirata; Etsuko Kobayashi, all of Kanagawa, Japan

[73] Assignee: Nitto Chemical Industry Co., Ltd., Tokyo, Japan

[21] Appl. No.: 764,295

[22] Filed: Dec. 12, 1996

Related U.S. Application Data

[63] Continuation of Ser. No. 191,214, Feb. 3, 1994, abandoned.

[30] Foreign Application Priority Data

| Feb. 3, 1993 | [JP] | Japan | 5-037276 |
| Sep. 8, 1993 | [JP] | Japan | 5-246028 |

[51] Int. Cl.⁶ .................................................. C12P 7/42
[52] U.S. Cl. ..................................... 435/146; 435/280
[58] Field of Search ................................ 435/146, 280

[56] References Cited

U.S. PATENT DOCUMENTS

| 5,223,416 | 6/1993 | Endo et al. | 435/128 |
| 5,283,193 | 2/1994 | Yamamoto et al. | 435/280 |
| 5,326,702 | 7/1994 | Endo et al. | 435/129 |

FOREIGN PATENT DOCUMENTS

| A20348901 | 1/1990 | European Pat. Off. ...... C12P 7/40 |
| 0449648 | 10/1991 | European Pat. Off. |
| 486289 | 5/1992 | European Pat. Off. |
| 3277292 | 12/1991 | Japan. |
| 4207197 | 7/1992 | Japan. |
| 5192190 | 8/1993 | Japan. |

OTHER PUBLICATIONS

*Applied and Environmental Microbiology*, vol. 57, No. 10 pp. 3028–3032 (1991).

*Primary Examiner*—Sandra E. Saucier
*Attorney, Agent, or Firm*—Sughrue, Mion, Zinn, Macpeak & Seas, PLLC

[57] ABSTRACT

A biological process for predominantly producing an optically active α-hydroxycarboxylic acid having a phenyl group directly from a racemic α-hydroxynitrile or a mixture of an aldehyde corresponding to the nitrile and prussic acid as a substrate is disclosed, comprising reacting a microorganism belonging to the genus Rhodococcus, Alcaligenes, Brevibacterium or Pseudomonas with the substrate in a neutral to basic aqueous medium. A desired optically active α-hydroxycarboxylic acid having a phenyl group can be obtained quantitatively at a high optical purity.

7 Claims, No Drawings

PROCESS FOR PRODUCING OPTICALLY ACTIVE α-HYDROXYCARBOXYLIC ACID HAVING PHENYL GROUP

This is a Continuation of application Ser. No. 08/191,214, filed Feb. 3, 1994 now abandoned.

FIELD OF THE INVENTION

This invention relates to a biological process for producing an optically active α-hydroxycarboxylic acid having a phenyl group. More particularly, it relates to a process for producing an optically active α-hydroxycarboxylic acid having a phenyl group as represented by formula (I) shown below, by the action of a microorganism capable of asymmetrically hydrolyzing a nitrile group of a racemic α-hydroxynitrile represented by formula (II) shown below. The optically active α-hydroxycarboxylic acid of formula (I) is of industrial importance as a starting material for synthesizing pharmaceuticals and agrochemicals, such as antibiotics, drugs acting on the sympathetic nervous system, anti-diabetic agents, and as a resolving reagent.

BACKGROUND OF THE INVENTION

Known processes for producing an optically active α-hydroxycarboxylic acid having a phenyl group include optical resolution of racemates by crystallization or chromatography and asymmetric synthesis through organochemical procedures. These processes generally involve complicated operations yet give only a low yield of a product.

To overcome these problems, biological processes utilizing microorganisms have been proposed. For example, it has been proposed to asymmetrically hydrolyze substituted or unsubstituted mandelonitrile or substituted or unsubstituted mandelamide by the action of a microorganism belonging to the genus Alcaligenes, Pseudomonas, Rhodopseudomonas, Corynebacterium, Acinetobacter, Bacillus, Mycobacterium, Rhodococcus or Candida to obtain optically active mandelic acid or a derivative thereof, as disclosed in European Patent Publication No. 0 384 901A (corresponding to JP-A-2-84198 (the term "JP-A" as used herein means an "unexamined published Japanese patent application")) and *Applied and Environmental Microbiology*, Vol. 57, pp. 3028–3032 (1991). It is also known to obtain a predominant proportion of R(−)-mandelic acid or a derivative thereof directly from racemic mandelonitrile or a derivative thereof by the action of a microorganism belonging to the genus Pseudomonas, Alcaligenes, Acinetobacter, Caseobacter, Nocardia, Bacillus, Brevibacterium or Aureobacterium as disclosed in U.S. Pat. No. 5,223,416 (corresponding to JP-A-4-218385, JP-A-4-99495 and JP-A-4-99496).

However, the above publications do not disclose producing an optically active α-hydroxycarboxylic acid having a phenyl group represented by formula (I) nor what activity the above microorganisms have relating to producing an optically active α-hydroxycarboxylic acid having a phenyl group represented by formula (I).

SUMMARY OF THE INVENTION

The present inventors searched extensively for a microorganism capable of producing an optically active α-hydroxycarboxylic acid having a phenyl group with industrial advantages. As a result, for such purposes, they found it effective to use a microorganism belonging to the genus Rhodococcus, Alcaligenes, Brevibacterium or Pseudomonas.

The present invention relates to a process for predominantly producing an optically active α-hydroxycarboxylic acid having a phenyl group, as represented by formula (I):

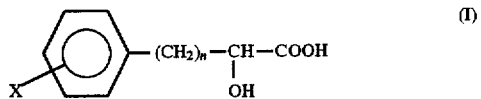

wherein X represents a hydrogen atom, a hydroxyl group, an aliphatic saturated alkyl group having from 1 to 3 carbon atoms, an aliphatic saturated alkoxy group having from 1 to 3 carbon atoms, a thioalkyl group, a halogen atom, a phenyl group, a phenoxy group, an amino group or a nitro group, which is bonded to the o-, m-, or p-position; and n represents 1 or 2, which comprises reacting a microorganism capable of asymmetrically hydrolyzing a nitrile group of a racemic α-hydroxynitrile represented by formula (II):

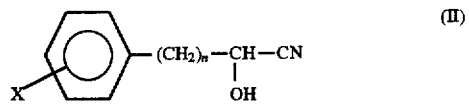

wherein X and n are as defined above, and wherein said microorganism belongs to the genus Rhodococcus, Alcaligenes, Brevibacterium or Pseudomonas or treated cells thereof with a racemic α-hydroxynitrile represented by formula (II) or a mixture of an aldehyde corresponding to said nitrile and prussic acid in a neutral to basic aqueous medium.

The present invention is based on the fact that the α-hydroxynitrile of formula (II) easily racemizes in a neutral to basic aqueous medium in the dissociation equilibrium between the α-hydroxynitrile and the corresponding aldehyde and prussic acid. The inventors found that the α-hydroxynitrile of formula (II) can be directly converted to an optically active α-hydroxycarboxylic acid having a phenyl group represented by formula (I) with predominance over a D-form or an L-form by coupling the above-mentioned racemization reaction with the above-mentioned microorganism. The term "with predominance" as used herein means that a D-form or an L-form is obtained from a racemic compound in a yield of from 50 to 100% based on the amount of reactant according to formula (II).

DETAILED DESCRIPTION OF THE INVENTION

The microorganism which can be used in the present invention belongs to the genus Rhodococcus, Alcaligenes, Brevibacterium or Pseudomonas and is capable of asymmetrically hydrolyzing a nitrile group of a racemic α-hydroxynitrile of formula (II) to produce and accumulate an optically active α-hydroxycarboxylic acid having a phenyl group, represented by formula (I), in high concentration.

The microorganism typically includes Rhodococcus sp. HT29-7 (FERM BP-3857) deposited Apr. 18, 1991, Alcaligenes sp. BC35-2 (FERM BP-3318) deposited Feb. 8, 1990, Alcaligenes sp. BC12-2 (FERM P-11263) deposited Feb. 8, 1990, Alcaligenes sp. BC20 (FERM P-11264) deposited Feb. 8, 1990, Alcaligenes sp. BC24 (FERM P-12063) deposited Mar. 1, 1991, Pseudomonas sp. BC-18 (FERM BP-4536) deposited Sep. 2, 1993, and Brevibacterium acetylicum (IAM 1790). Of these microorganisms, Rhodococcus sp. HT29-7, Alcaligenes sp. BC35-2, BC12-2, BC20 and BC24, and Pseudomonas sp. BC-18 are novel strains which the inventors isolated from soil and deposited with National Institute of Bioscience & Human Technology (formerly, Fermentation Research Institute), Agency of Industrial Science & Technology under the respective deposit receipt numbers. Morphological and physiological properties of these strains are described below. *Brevibacterium acetylicum* IAM 1790 is a known strain and available at Institute of Applied Microbiology, The University of Tokyo (IAM).

HT29-7:

| | |
|---|---|
| Shape: | polymorphic bacillus |
| Gram's stain: | + |
| Spore: | − |
| Motility: | − |
| Color of colony: | pink to orange |
| Rod-coccus cycle: | + |
| Extension of peripheral cells of colony: | observed |
| Formation of aerial hypha | not observed |
| Oxidase: | − |
| Catalase: | + |
| Behavior toward oxygen | aerobic |
| Diamino acid of cell wall: | meso-diaminopimelic acid |
| Glycolyl test: | + (glycolyl type) |
| Sugar composition of cell wall: | |
| Arabinose: | + |
| Galactose: | + |
| Existence of quinone: | MK-9 (H$_2$) |

BC35-2, BC12-2, BC20, and BC24:

| | |
|---|---|
| Shape: | bacillus |
| Gram's stain: | − |
| Spore: | − |
| Motility: | + |
| Flagellum: | peripheral |
| Oxidase: | + |
| Catalase: | + |
| OF test: | alkalization |
| Production of 3-ketolactose: | − |
| Existence of quinone: | Q-8 |

BC-18:

| | |
|---|---|
| Shape: | bacillus |
| Gram's stain: | − |
| Spore: | − |
| Motility: | + |
| Flagellum: | polar |
| Oxidase: | + |
| Catalase: | + |
| OF test: | 0 |

The above-described taxonomical properties were examined by referring to *Bergey's Manual of Systematic Bacteriology* (1986). The HT29-7 strain belongs to the genus Rhodococcus; BC35-2, BC12-2, BC20 and BC24 strains belong to the genus Alcaligenes; and the BC-18 strain belongs to the genus Pseudomonas.

Typical examples of the compounds of formula (II) which can be used as a substrate in the present invention include phenyllactonitrile, 4-phenyl-α-hydroxybutyronitrile, 3-(2-methoxyphenyl)-lactonitrile, 3-(3-methoxyphenyl)-lactonitrile, 3-(4-methoxyphenyl)-lactonitrile, 4-(4-fluorophenyl)-α-hydroxybutyronitrile, 4-(2-chlorophenyl)-α-hydroxybutyronitrile, 4-(4-bromophenyl)-α-hydroxybutyronitrile, 4-(2-trifluoromethylphenyl)-α-hydroxybutyronitrile, 4-(3-trifluoromethylphenyl)-α-hydroxybutyronitrile and 4-(2-hydroxyphenyl)-α-hydroxybutyronitrile.

Cultivation of the microorganism is carried out by using usual media containing assimilable carbon sources (e.g., glycerol, glucose, saccharose, malt extract, lactose, and fructose); assimilable nitrogen sources (e.g., casamino acid, meat extract, and yeast extract); and inorganic nutrients essential for growth (magnesium chloride, sodium sulfate, calcium chloride, manganese sulfate, iron chloride, and zinc sulfate).

To obtain increased enzyme activity, an enzyme inducer preferably is added to the culture medium in the initial or middle stage of cultivation, in such a concentration as not to significantly inhibit growth. Suitable enzyme inducers include nitriles (e.g., cinnamonitrile, benzyl cyanide, isobutyronitrile, β-phenylpropionitrile, benzonitrile, 2-, 3- or 4-cyanopyridine, 1-cyclohexenylacetonitrile, ε-caprolactam, γ-butyronitrile, and o-aminobenzonitrile); and amides (e.g., isobutylamide, phenylacetamide, and 4-pyridinecarboxylic acid amide).

Culturing is aerobically conducted at a pH of 4 to 10 and a temperature of 5° to 50° C., for a period of about 1 to 7 days, until the maximum activity is reached.

The asymmetric hydrolysis reaction can be carried out by suspending microbial cells harvested from the culture or treated microbial cells (e.g., dried cells, ruptured cells, a crude or purified isolated enzyme, immobilized microbial cells or an immobilized enzyme) in an aqueous medium (e.g., water and a buffer solution), and bringing a racemic β-hydroxynitrile of formula (II) or a mixture of an aldehyde corresponding to the nitrile and prussic acid into contact with the cell suspension. The reaction system should be maintained near neutral or basic in order to racemize the α-hydroxynitrile of formula (II). That is, the pH of the reaction system should be kept within a range of 6 to 11, and preferably 7 to 10.

The concentration of the substrate in the reaction system usually ranges from 0.1 to 10% by weight, and preferably from 0.2 to 5.0% by weight in terms of the racemic α-hydroxynitrile of formula (II), while varying depending on sensitivity of the enzyme to the aldehyde corresponding to the racemic α-hydroxynitrile of formula (II) or prussic acid.

To reduce enzyme denaturation by an aldehyde, sodium sulfite, acid sodium sulfite, sodium dithionite, potassium sulfite, acid potassium sulfite, potassium dithionite, ammonium sulfite, acid ammonium sulfite, or ammonium dithionite in an amount of 1 to 1000 mM may be added.

The microorganism usually is used in an amount of 0.01 to 5.0% by weight on a dry basis based on the substrate. The reaction usually is conducted at a temperature of 0° to 50° C., and preferably 10° to 30° C., for a period of 0.1 to 100 hours.

The reaction product, i.e., an optically active α-hydroxycarboxylic acid of formula (I), can be isolated from the reaction mixture by known procedures. For example, the microbial cells may be removed by centrifugation, and if desired, granular components, proteins, and polysaccharides may be removed by ultrafiltration or the like. The supernatant may be treated with activated carbon. Then, the supernatant is concentrated under reduced pressure or extracted with an organic solvent in an acidic condition, followed by repeated recrystallization from benzene, etc. to obtain a high purity crystal.

The present invention provides an industrially excellent process for preparing an optically active α-hydroxycarboxylic acid having a phenyl group represented by formula (I) at almost quantitative selectivity and at high optical purity.

The present invention will now be illustrated in greater detail with reference to Examples, but it should be understood that the present invention is not deemed to be limited thereto. All percentages are by weight unless otherwise indicated.

EXAMPLE 1

Preparation of L-3-Phenyllactic Acid (1) Culturing:

Rhodococcus sp. HT29-7 (FERM BP-3857), Alcaligenes sp. BC35-2 (FERM BP-3318) or *Brevibacterium acetylicum* IAM 1790 was aerobically cultured in a medium having the following composition, with 0.05% benzyl cyanide added as an inducer, at 30° C. for 72 hours.

| Medium Composition: | |
|---|---|
| Glycerol | 20 g |
| Yeast extract | 3 g |
| Potassium primary phosphate | 6.8 g |
| Sodium secondary phosphate | 7.1 g |
| Sodium sulfate | 2.8 g |
| Magnesium chloride | 0.4 g |
| Calcium chloride | 0.04 g |
| Manganese sulfate | 0.03 g |
| Iron chloride | 0.006 g |
| Zinc sulfate | 0.003 g |
| Distilled water | 1000 ml |
| pH = 7.5 | |

(2) Asymmetric Hydrolysis:

Microbial cells harvested from the culture were washed with a 50 mM phosphoric acid buffer solution (pH=8.2) by centrifugation and suspended in the same buffer solution containing 10 mM phenyllactonitrile at such a cell concentration as to have an optical density at 630 nm ($OD_{630}$) of 20. The cell suspension was allowed to react at 30° C. for hours while shaking.

After completion of the reaction, the microbial cells were removed by centrifugation. The content of phenyllactic acid in the supernatant was determined by liquid chromatography (column: Wakosil ODS 5C18; carrier solution: 0.1M phosphoric acid:acetonitrile=3:1 by volume; monitor: 254 nm). The supernatant was adjusted to pH 12 with 6N NaOH and extracted twice with an equal amount of ethyl acetate to remove any unreacted phenyllactonitrile. The aqueous layer was adjusted to pH 1.2 with sulfuric acid and extracted twice with an equal amount of ethyl acetate. The extract was evaporated to dryness in an evaporator, and the residue was dissolved in water and analyzed on an optical resolution column (MCI gel CRS-10W; carrier solution: 2 mM $CuSO_4.5H_2O$:acetonitrile=85:15 by volume). The results obtained are shown in Table 1 below.

TABLE 1

| Microorganism | Yield (mM) | Optical Purity (L-Form) (% ee) |
|---|---|---|
| HT29-7 | 6.0 (60%) | 60 |
| BC35-2 | 0.55 (5.5%) | 45 |
| IAM 1790 | 9.9 (99%) | 10 |

EXAMPLE 2

Preparation of L-3-Phenyllactic Acid

Microbial cells of HT29-7 strain or IAM 1790 strain harvested in the same manner as in Example 1 were suspended in a phosphoric acid buffer solution (pH=8.2) containing 10 mM phenylaldehyde and 10 mM potassium cyanide to a cell concentration of $OD_{630}$=20. The cell suspension was allowed to react at 30° C. for 96 hours with shaking.

The reaction mixture was worked-up in the same manner as in Example 1. The phenyllactic acid content and its optical purity were determined in the same manner as in Example 1, with the results shown in Table 2 below.

TABLE 2

| Microorganism | Yield (mM) | Optical Purity (L-Form) (% ee) |
|---|---|---|
| HT29-7 | 7.1 (71%) | 64 |
| IAM 1790 | 9.8 (98%) | 14 |

EXAMPLE 3

Preparation of L-4-Phenyl-α-hydroxybutyric Acid

Microbial cells of HT29-7 strain harvested in the same manner as in Example 1 were suspended in a phosphoric acid buffer solution (pH=8.2) containing 10 mM 4-phenyl-α-hydroxybutyronitrile to a concentration of $OD_{630}$=20. The cell suspension was allowed to react at 30° C. for 96 hours with shaking. Further, the same reaction was carried out in the presence of 100 mM sodium sulfite for reducing enzyme denaturation by the aldehyde.

The reaction mixture was worked-up in the same manner as in Example 1. The 4-phenyl-α-hydroxybutyric acid content and the optical purity were determined in the same manner as in Example 1, with results shown in Table 3 below.

TABLE 3

| Microorganism | Sodium Sulfite | Yield (mM) | Optical Purity (L-Form) (% ee) |
|---|---|---|---|
| HT29-7 | not added | 9.4 (94%) | 87 |
| " | added | 9.9 (99%) | 91 |

EXAMPLE 4

Preparation of L-3-Phenyllactic Acid (1) Culturing:

Pseudomonas sp. BC-18 (FERM BP-4536) was aerobically cultured in a medium having the following composition, with 0.03% 1-cyclohexenylacetonitrile added as an inducer, at 30° C. for 3 days.

Medium Composition:

| Glycerol | 20 g |
|---|---|
| Yeast extract | 6 g |
| Metal salt mixed solution* | 5 ml |
| 1M Sodium sulfate | 2 ml |
| 50 mM Phosphoric acid buffer solution (pH = 7.5) | 993 ml |

*Sodium sulfate (56 g), magnesium chloride (8 g), calcium chloride (0.8 g), manganese sulfate (0.6 g), iron chloride (0.12 g) and zinc sulfate (0.06 g) in distilled water (100 ml)

(2) Asymmetric Hydrolysis:

Microbial cells harvested from the culture were washed with a 50 mM phosphoric acid buffer solution (pH=7.5) by centrifugation and suspended in a phosphoric acid buffer solution having a prescribed pH and containing 20 mM phenyllactonitrile at a cell concentration of $OD_{630}$=29.0. The cell suspension was allowed to react at 30° C. for 24 hours while shaking.

After completion of the reaction, the microbial cells were removed by centrifugation. The content of phenyllactic acid in the supernatant was determined by liquid chromatography (column: Wakosil ODS 5C18; carrier solution: 0.1M phosphoric acid:acetonitrile=7:3 by volume; monitor: 254 nm). The supernatant was adjusted to pH 9.0 with 6N NaOH and extracted twice with an equal amount of ethyl acetate to remove any unreacted phenyllactonitrile. The aqueous layer was adjusted to pH 2.0 with sulfuric acid and extracted twice with an equal amount of ethyl acetate. The extract was evaporated to dryness in an evaporator, and the residue was dissolved in water and analyzed on an optical resolution column (MCI gel CRS-10W; carrier solution: 2 mM $CuSO_4 \cdot 5H_2O$:acetonitrile=85:15 by volume). The results obtained are shown in Table 4 below.

TABLE 4

| Microorganism | pH | Yield (mM) | Optical Purity (L-Form) (% ee) |
|---|---|---|---|
| BC-18 | 6.0 | 12.37 (61.9%) | 21.1 |
| " | 6.5 | 11.35 (56.8%) | 42.5 |
| " | 7.0 | 11.15 (55.8%) | 48.0 |
| " | 7.5 | 11.00 (55.0%) | 63.8 |
| " | 8.0 | 11.02 (55.1%) | 61.4 |
| " | 8.5 | 14.05 (70.3%) | 74.1 |
| " | 9.0 | 13.90 (69.5%) | 73.8 |

While the invention has been described in detail and with reference to specific examples thereof, it will be apparent to one skilled in the art that various changes and modifications can be made therein without departing from the spirit and scope thereof.

What is claimed is:

1. A process for predominantly producing an optically active α-hydroxycarboxylic acid having a phenyl group as represented by formula (I):

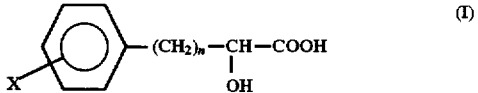
(I)

wherein X represents a hydrogen atom, a hydroxyl group, an aliphatic saturated alkyl group having from 1 to 3 carbon atoms, an aliphatic saturated alkoxy group having from 1 to 3 carbon atoms, a thioalkyl group, a halogen atom, a phenyl group, a phenoxy group, an amino group or a nitro group, which is bonded to the o-, m-, or p-position; and n represents 1 or 2, which comprises reacting a microorganism capable of asymmetrically hydrolyzing a nitrile group of a racemic α-hydroxynitrile represented by formula (II):

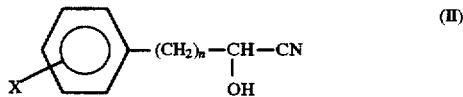
(II)

wherein X and n are as defined above, wherein said microorganism is selected from the group consisting of Rhodococcus sp. HT29-7 (FERM BP-3857), Alcaligenes sp. BC12-2 (FERM-P-11263), Alcaligenes sp. BC20 (FERM P-11264), Alcaligenes sp. BC24 (FERM P-12063), Pseudomonas sp. BC18 (FERM BP-4536), *Brevibacterium acetylicum* (IAM 1790), and treated cells thereof with a racemic α-hydroxynitrile represented by formula (II) or a mixture of an aldehyde corresponding to said nitrile and prussic acid in a neutral to basic aqueous medium, and recovering the optically active α-hydroxycarboxylic acid having a phenyl group; wherein the yield of the compound according to formula (I) is 55 to 100% based on the amount of the α-hydroxynitrile according to formula (II).

2. The process as claimed in claim 1, wherein α-hydroxynitrile is phenyllactonitrile, 4-phenyl-α-hydroxybutyronitrile, 3-(2-methoxyphenyl)-lactonitrile, 3-(3-methoxyphenyl)-lactonitrile, 3-(4-methoxyphenyl)-lactonitrile, 4-(4-fluorophenyl)-α-hydroxybutyronitrile, 4-(2-chlorophenyl)-α-hydroxybutyronitrile, 4-(4-bromophenyl)-α-hydroxybutyronitrile, 4-(2-trifluoromethylphenyl)-α-hydroxybutyronitrile, 4-(3-trifluoromethylphenyl)-α-hydroxybutyronitrile and 4-(2-hydroxyphenyl)-α-hydroxybutyronitrile.

3. The process as claimed in claim 1, wherein the reaction occurs in a system having a pH of 6 to 11.

4. The process as claimed in claim 1, wherein the microorganism is Rhodococcus sp. HT29-7 (FERM BP-3857).

5. The process as claimed in claim 1, wherein the microorganism is Alcaligenes sp. BC12-2 (FERM-P-11263) or sp. BC20 (FERM P-11264) or sp. BC24(FERM P-12063).

6. The process as claimed in claim 1, wherein the microorganism is *Brevibacterium acetylicum* (IAM 1790).

7. The process as claimed in claim 1, wherein the microorganism is Pseudomonas sp. BC18 (FERM BP-4536).

* * * * *